(12) United States Patent
Multhoff

(10) Patent No.: US 7,396,681 B1
(45) Date of Patent: Jul. 8, 2008

(54) APPLICATION OF HSP70 PROTEINS

(76) Inventor: Gabriele Multhoff, Kirchenstrasse 17c, 81675 München (DE)

( * ) Notice: Subject to any disclaimer, the term of this patent is extended or adjusted under 35 U.S.C. 154(b) by 0 days.

(21) Appl. No.: 09/646,835

(22) PCT Filed: Mar. 29, 1999

(86) PCT No.: PCT/EP99/02165

§ 371 (c)(1),
(2), (4) Date: Jan. 11, 2001

(87) PCT Pub. No.: WO99/49881

PCT Pub. Date: Oct. 7, 1999

(30) Foreign Application Priority Data

Mar. 27, 1998 (DE) ................. 198 13 760
Mar. 26, 1999 (WO) ............ PCT/EP99/02056

(51) Int. Cl.
*C12N 5/00* (2006.01)
(52) U.S. Cl. .............. 435/373; 435/325; 435/366; 435/372; 424/937; 424/937.1
(58) Field of Classification Search ................ 435/375, 435/383, 384, 372; 424/277.1, 278.1, 93.7, 424/93.71; 514/12, 21; 530/350
See application file for complete search history.

(56) References Cited

U.S. PATENT DOCUMENTS 5,348,945 A    9/1994  Berberian et al.
6,261,839 B1 *  7/2001  Multhoff et al.

FOREIGN PATENT DOCUMENTS

| EP | 0 584 715 B1 |   | 3/1994 |
| EP | 0 843 005    |   | 11/1997 |
| WO | WO 91/15219  |   | 10/1991 |
| WO | WO 93/21529  |   | 10/1993 |
| WO | WO 95/03418  |   | 2/1995 |
| WO | WO 97/10001  | * | 3/1997 |

OTHER PUBLICATIONS

Multhoff et al (Journal of Immunology, 1997, vol. 158, pp. 4341-4350).*
Botzler et al (Cell Stress and chaperones, 1998, vol. 3, pp. 6-11), abstract.*
Multhoff et al (Blood, 1995, vol. 86, pp. 1374-1382).*
Lazar et al. Molecular and Cellular Biology 8:1247-1252, 1988.*
Burgess et al, J of Cell Bio. 111:2129-2138, 1990.*
Suzuki, S. et al., IL-12 Induced Enhancement . . . On Cancer Cells, Proceedings of the American Association For Cancer Research, vol. 37, p. 445, 1996.
Yasuaki Tamura, Ping Peng, Kang Liu, Maria Daou, Pramod K Srivastava; Immunotherapy of Tumors with Autologous Tumor-Derived Heat Shock Protein Preparations; Oct. 3, 1997 Science vol. 278, 117-120.
Gabriele Multhoff, Claus Botzler, Marion Wiesnet, Gunther EiBner and Rolf Issels; CD3 Large Granular Lymphocytes Recognize a Heat-Inducible Immunogenic Determinant Associated With the 72-kD Heat Shock Protein on Human Sarcoma Cells; Blood, vol. 86, Mar. 28, 1995; (pp. 1374-1382).
Heiichiro Udono and Pramod K Srivastava; Comparison of Tumor-Specific Immunogenicities of Stress-Induced Proteins gp96, hsp90, and hsp70[1]; J. of Immunology, vol. 152, No. 11, pp. 5398-5403, 1994.
Claus Botzler, Gloria Li, Rolf D. Issels and Gabriele Multhoff; Definition of extracellular Localized Epitopes of Hsp70 Involved in an NK Immunue Response, Cell Stress & Chaperones, vol. 3, No. 1 (1998) (pp. 6-11).
Gabriele Multhoff, Claus Botzler and Rolf Issels, The Role of Heat Shock Proteins In the Stimulation of An Immune Response; Biol. Chem. vol. 379, (pp. 295-300), Mar. 1998.
Savary et al., Role of Heat Shock Proteins in Immunity to Breast Cancer, Breast Cancer Research and Treatment, V. 46, No. 1, p. 69, 1997.
Multhoff & Botzler, Heat-Shock Proteins and the Immune Response, Annals of the New York Academy of Sciences, vol. 851, pp. 86-93, 1998.
Wang, et al. "Heat Shock Proteins And Cancer Immunotherapy", Immunological Investigations (2000) pp. 131-137, vol. 29(2).
MULTIMMUNE Internet Homepage, "www.multimmune.de".

* cited by examiner

*Primary Examiner*—Christopher Yaen

(57) ABSTRACT

The invention relates to the use of Hsp70 protein or fragments thereof for the activation of NK-cells, pharmaceutical preparations, medical product or medical adjuvants containing a Hsp70 protein or fragments thereof or activated cells, method for the activation of NK-cells as well as medical use of the products obtained by the method of the invention.

22 Claims, 8 Drawing Sheets

Figure 1A:
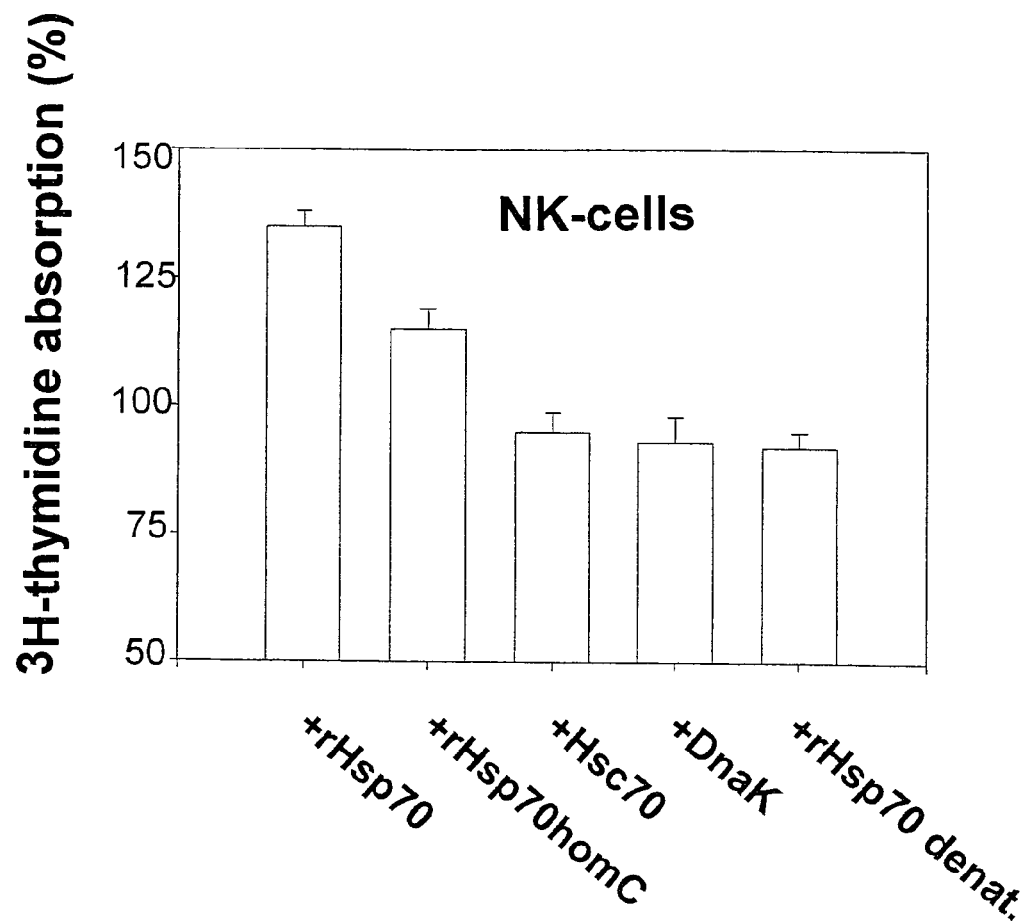

Growth of NK-cells increased by rHsp70, rHsp70-C$_{term}$ and rHsp70homC

Increase in the growth of T-cells exclusively by Dnak (=E. coli Hsp70)

Recombinant Hsp70-protein increases the lysis of CX+ tumour cells (which have Hsp70 on the membrane)

Recombinant Hsp70-protein does not increase the lysis of CX- tumour cells (no Hsp70-membrane expression)

Intact Hsp70-protein with display of the C-terminal region necessary for the NK-stimulation.

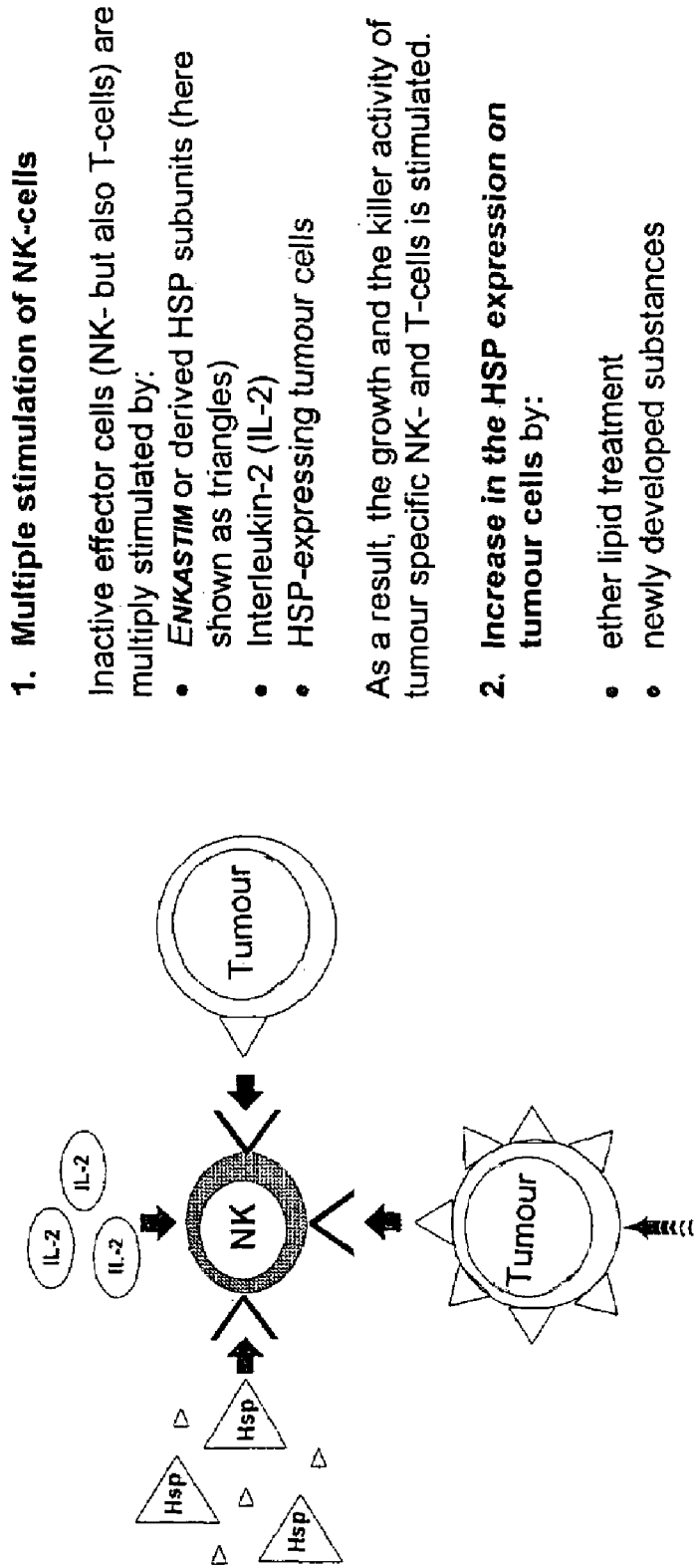

FIG. 6

1. Multiple stimulation of NK-cells

Inactive effector cells (NK- but also T-cells) are multiply stimulated by:
   - ENKASTIM or derived HSP subunits (here shown as triangles)
   - Interleukin-2 (IL-2)
   - HSP-expressing tumour cells As a result, the growth and the killer activity of tumour specific NK- and T-cells is stimulated.

2. Increase in the HSP expression on tumour cells by:
   - ether lipid treatment
   - newly developed substances

SEQUENCE LISTING

```
<160> NUMBER OF SEQ ID NOS: 2

<210> SEQ ID NO 1
<211> LENGTH: 641
<212> TYPE: PRT
<213> ORGANISM: homo sapiens
<300> PUBLICATION INFORMATION:
<301> AUTHORS: Milner, Caroline M.
<302> TITLE: Structure and Expression of the Three MHC-Linked HSP70
      Genes
<303> JOURNAL: Immunogenetics
<304> VOLUME: 32
<305> ISSUE: 4
<306> PAGES: 242-251
<307> DATE: 1990
<313> RELEVANT RESIDUES: 384 TO 561

<400> SEQUENCE: 1

Met Ala Lys Ala Ala Ala Ile Gly Ile Asp Leu Gly Thr Thr Tyr Ser
  1               5                  10                  15

Cys Val Gly Val Phe Gln His Gly Lys Val Glu Ile Ile Ala Asn Asp
                 20                  25                  30

Gln Gly Asn Arg Thr Thr Pro Ser Tyr Val Ala Phe Thr Asp Thr Glu
             35                  40                  45

Arg Leu Ile Gly Asp Ala Ala Lys Asn Gln Val Ala Leu Asn Pro Gln
         50                  55                  60

Asn Thr Val Phe Asp Ala Lys Arg Leu Ile Gly Arg Lys Phe Gly Asp
 65                  70                  75                  80

Pro Val Val Gln Ser Asp Met Lys His Trp Pro Phe Gln Val Ile Asn
                 85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
```

-continued

```
                225                 230                 235                 240
        Phe Val Glu Glu Phe Lys Arg Lys His Lys Lys Asp Ile Ser Gln Asn
                        245                 250                 255

Lys Arg Ala Val Arg Arg Leu Arg Thr Ala Cys Glu Arg Ala Lys Arg
                        260                 265                 270

Thr Leu Ser Ser Ser Thr Gln Ala Ser Leu Glu Ile Asp Ser Leu Phe
                        275                 280                 285

Glu Gly Ile Asp Phe Tyr Thr Ser Ile Thr Arg Ala Arg Phe Glu Glu
                        290                 295                 300

Leu Cys Ser Asp Leu Phe Arg Ser Thr Leu Glu Pro Val Glu Lys Ala
        305                 310                 315                 320

Leu Arg Asp Ala Lys Leu Asp Lys Ala Gln Ile His Asp Leu Val Leu
                        325                 330                 335

Val Gly Gly Ser Thr Arg Ile Pro Lys Val Gln Lys Leu Leu Gln Asp
                        340                 345                 350

Phe Phe Asn Gly Arg Asp Leu Asn Lys Ser Ile Asn Pro Asp Glu Ala
                        355                 360                 365

Val Ala Tyr Gly Ala Ala Val Gln Ala Ala Ile Leu Met Gly Asp Lys
                        370                 375                 380

Ser Glu Asn Val Gln Asp Leu Leu Leu Leu Asp Val Ala Pro Leu Ser
        385                 390                 395                 400

Leu Gly Leu Glu Thr Ala Gly Gly Val Met Thr Ala Leu Ile Lys Arg
                        405                 410                 415

Asn Ser Thr Ile Pro Thr Lys Gln Thr Gln Ile Phe Thr Thr Tyr Ser
                        420                 425                 430

Asp Asn Gln Pro Gly Val Leu Ile Gln Val Tyr Glu Gly Glu Arg Ala
                        435                 440                 445

Met Thr Lys Asp Asn Asn Leu Leu Gly Arg Phe Glu Leu Ser Gly Ile
                        450                 455                 460

Pro Pro Ala Pro Arg Gly Val Pro Gln Ile Glu Val Thr Phe Asp Ile
        465                 470                 475                 480

Asp Ala Asn Gly Ile Leu Asn Val Thr Ala Thr Asp Lys Ser Thr Gly
                        485                 490                 495

Lys Ala Asn Lys Ile Thr Ile Thr Asn Asp Lys Gly Arg Leu Ser Lys
                        500                 505                 510

Glu Glu Ile Glu Arg Met Val Gln Glu Ala Lys Tyr Lys Ala Glu
                        515                 520                 525

Asp Glu Val Gln Arg Glu Arg Val Ser Ala Lys Asn Ala Leu Glu Ser
                        530                 535                 540

Tyr Ala Phe Asn Met Lys Ser Ala Val Glu Asp Glu Gly Leu Lys Gly
        545                 550                 555                 560

Lys Ile Ser Glu Ala Asp Lys Lys Val Leu Asp Lys Cys Gln Glu
                        565                 570                 575

Val Ile Ser Trp Leu Asp Ala Asn Thr Leu Ala Glu Lys Asp Glu Phe
                        580                 585                 590

Glu His Lys Arg Lys Glu Leu Glu Gln Val Cys Asn Pro Ile Ile Ser
                        595                 600                 605

Gly Leu Tyr Gln Gly Ala Gly Gly Pro Gly Pro Gly Gly Phe Gly Ala
                        610                 615                 620

Gln Gly Pro Lys Gly Gly Ser Gly Ser Gly Pro Thr Ile Glu Glu Val
        625                 630                 635                 640

Asp
```

```
<210> SEQ ID NO 2
<211> LENGTH: 7
<212> TYPE: PRT
<213> ORGANISM: homo sapiens

<400> SEQUENCE: 2

Asn Leu Leu Gly Arg Phe Glu
 1               5
```

APPLICATION OF HSP70 PROTEINS

The invention relates to the use of Hsp70 protein or fragments thereof for the activation of NK-cells, pharmaceuticals, medical products or medical adjuvants which contain a Hsp70 protein or fragments thereof or activated NK-cells, a method for the activation of NK-cells as well as medical uses of the products obtained by the method of the invention.

Chaperones are necessary for a number of fundamental processes in the cell. In particular, it is known that they counteract cell stress. The best analysed class of chaperones is the group of the heat-shock proteins (HSP) with a molecular weight of 70 kDa (Multhoff et al., Cell Stress & Chaperones 1 (3) (1996), 167). These proteins are highly preserved in an evolutionary way. They bind to unfolded or incorrectly folded polypeptides in the cell, stabilize them and in that way inhibit their aggregation or make it possible for a transmembrane translocation to take place. Hsp70 is localized in the nucleus, in the cytosol and on the cell surface of certain tumour cells. Apart from their intracellular task as chaperones the members of the Hsp70 family seem to play a role as to the stimulation of the immune system, e.g. inflammatory processes under participation of pathogens, and as to the cellular anti-tumour immune response in vivo and in vitro. Accordingly, a range of therapeutic uses of heat-shock proteins has been presented in the state of the art. In WO 97/10000, the use of complexes consisting of a heat-shock protein and an exogenous antigen molecule (peptide) bound to this protein in a non-covalent way is described for the prevention and treatment of tumour and infectious diseases. The antigens present with the heat-shock proteins in the complex derive from tumour cells. They have the same characteristic, i.e. both induce an immune response. Multhoff et al., Biol. Chem. 379 (1998), 295-300 assign a role to HSPs, including Hsp70, in the recognition of non-MHC-restricted effector cells, including NK-cells. In particular, it was found that NK-cells recognise Hsp70 molecules present on the surface of tumour cells and then lyse the tumour cells. Another approach of therapy for cancer diseases has been introduced by Tamura and colleagues (Tamural et al., Science 278 (1997), 117-123). They were able to demonstrate that tumour-carrying mice can be treated successfully with heat-shock preparations if derived from autologous tumours. Preparations from non-autologous tumours or from normal tissue, however, do not lead to the regression of the tumours (Blachere et al., J. Exp. Med. 186 (1997) 1315-1322). In the study by Tamura et al., the HSPs form complexes with a number of peptides which have not been identified in more detail. To sum up one can say that the state of the art shows an immunological activity of HSP molecules if they either form complexes with peptides and/or are present on the surface of cells such as tumour cells. Thus, although the potential of heat-shock proteins basically has been recognised for fighting various diseases, the successful therapeutic use usually depends on the preparation of certain complexes or cell preparations as well as the amount of the starting material (tumour material): It is hard to imagine a universal or patient-independent use of these complexes or cell preparations.

Thus, the problem underlying the present invention was to provide new means and methods for the use of the immunological potential of heat-shock proteins which do not have the above-mentioned disadvantages of the state of the art.

This problem has been solved by providing the embodiments characterised in the claims.

Therefore, the invention relates to the use of a Hsp70 protein, a carboxy-terminal (C-terminal) fragment thereof or a derivative thereof or a protein with an amino acid sequence homology to the C-terminal region of the Hsp70 protein of $\geq 70\%$ for the production of a pharmaceutical preparation, medical product or a medical adjuvant for the activation of NK-cells.

According to the invention, pharmaceutical preparations are defined as substances and preparations of substances which, when used on or in the human body, are meant for healing, alleviating, preventing or recognising diseases, ailments, physical defects or pathological discomforts.

According to the invention, medical products are all substances or preparations used individually or in combination with each other of substances, or other subject-matters which, according to the producer, are meant to be applied to humans due to their functions for the purpose of detecting, preventing, monitoring, treating or alleviating diseases and whose main effect in or on the human body is achieved neither by pharmacologically or immunologically effective preparations nor by a metabolism whose effectiveness may well be supported by such preparations.

According to the invention, medical adjuvants are such substances which are used for the production (as active ingredients) of pharmaceutical preparations.

Moreover, the invention relates to the use of a Hsp70 protein, a C-terminal fragment thereof or a derivative thereof or a protein with an amino acid sequence homology to the C-terminal region (amino acids 384-641) of the Hsp70 protein of $\geq 70\%$ for ex vivo or in vitro activation of NK-cells.

Figure 5:
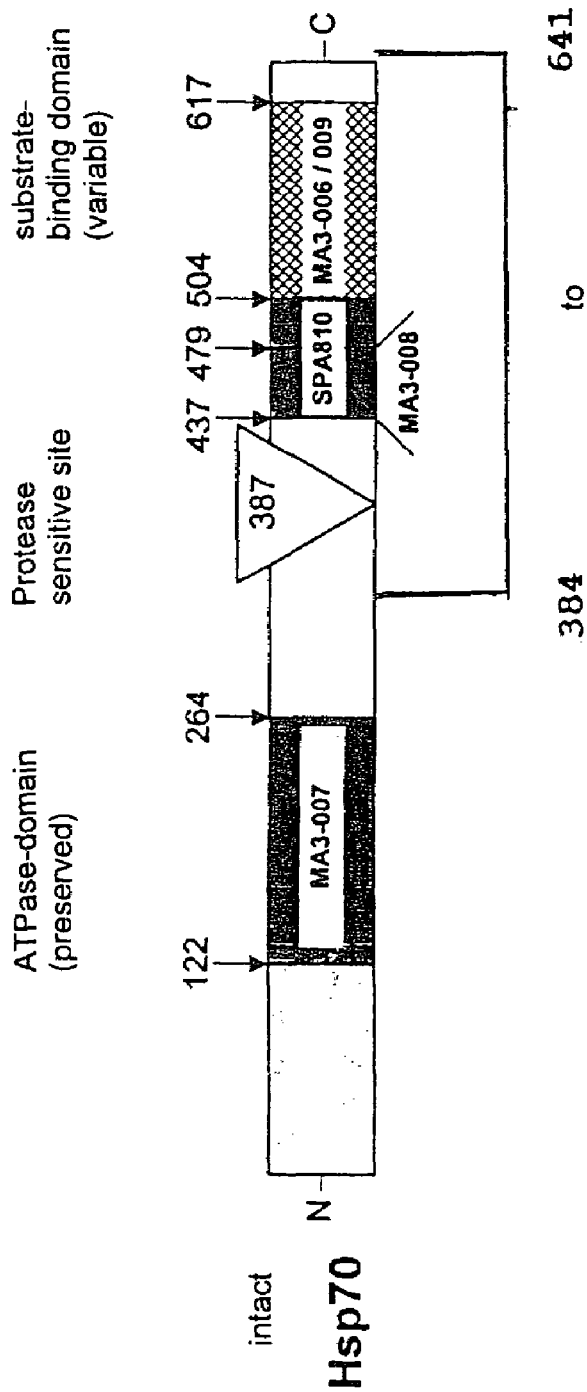

According to the invention, the term "Hsp70 protein" relates to eukaryotic heat-shock proteins, the expression of which can be induced by heat but also by a number of other reagents such as e.g. amino acid analogues, heavy metals, ionophores or cytotoxines, wherein the factor of the increase in the expression by means of induction is at least 5, compared to the constitutive expression. The enclosed FIG. 5 shows the composition of a Hsp70 protein comprising an N-terminal ATPace domain and a C-terminal substrate-binding domain of the protein. The complete amino acid sequence has been published in Milner et al., Immunogenetics 32 (4) (1990), 242-251.

According to the invention, the term "carboxy-terminal (C-terminal) fragment" of the Hsp70 protein comprises (poly)peptides exhibiting an amino acid sequence from the range of amino acids 384-641 of the human Hsp70. The present invention also comprises fragments of the C-terminal fragment 384-641. In further embodiments the term comprises (poly)peptides derived from the region of another protein that is also comprised in the term "Hsp70 protein" used according to the invention, this region being homologous to the above-mentioned C-terminal region of the human Hsp70 protein. The fragments of the Hsp70 protein used according to the invention are also able to activate NK-cells. The activation can easily be verified by the person skilled in the art by means of the teaching of the invention. Thus, the person skilled in the art is also able to produce fragments from the above-mentioned fragment 384-641 by recombinant techniques without further ado (standard methods for this are described in Sambrook et al., "Molecular Cloning, A Laboratory Manual", 2. edition 1989, CSH Press, Cold Spring Harbor, N.Y.) and test them for the activation properties wanted.

The term "derivate" comprises both derivatives of the Hsp70 protein as well as derivatives of the C-terminal fragment as far as the derivatives exhibit the functions of the invention. Preferably, such derivatives exhibit the same three-dimensional structure as Hsp70 or its C-terminal fragment and can be produced, for example, by peptidomimetics (al-Obeidi et al., Mol. Biotechnol. 9 (1998), 205-223; Wiley et al., Med. Res. Rev. 13 (1993), 327-384; Bohm, J. Comput. Aided Mol. Des. 10 (1996), 265-272; Hruby et al., Biopolymers 43 (1997), 219-266).

The term "NK-cells" ("natural killer cells") comprises big, granular lymphocytes expressing CD45 on the surface and exhibiting killer activity without prior stimulation. They are particularly characterised in that they express CD16 and/or can be stimulated by interleukin-2 and/or do not express CD3 and/or do not have $\alpha/\beta$- or $\gamma/\delta$-T-cell receptors.

The NK-cells developing their effectiveness in the method of the invention are further characterised by the following properties:
- they are transient plastic-adherent after addition of IL-2 in amounts of 10 to 10,000 Units, e.g. of 100 I U, wherein IL-2 can be purchased from the firm Chiron;
- the adherence takes effect 3-18 hours after addition of IL-2 on newly isolated PBL (peripheral blood lymphocytes depleted by monocytes);
- the NK-cells exhibit a CD16dim expression (average value of fluorescence weak);
- the NK-cells express CD56 and CD57 as typical NK marker;
- the NK-cells express CD94 (C-type lectin killer cell receptor)
- the NK-cells secrete after activation with Hsp70 and cytokins IFNgamma;
- the NK-cells can be stimulated by addition of Hsp70 (purified protein) (growth and cytotoxic activity);
- they are not dependent on the patient's MHC type.

According to the invention, other NK-cell populations can be used, too. In this case, however, it is a pre-requisite that they can be activated by the Hsp70 used according to the invention or by the above-mentioned fragments or derivatives. According to the invention, isolated NK-cells can be used. It is furthermore possible to use cell mixtures such as peripheral mononucleic blood cells (PBMC) containing NK-cells.

According to the invention, the term "amino acid sequence homology to the C-terminal region of the Hsp70 protein$\geq$70%" means that at least 70% of the amino acids are identical when two amino acid sequences are aligned, wherein one of the aligned amino acid sequences is the one of the C-terminal region of Hsp70. It also comprises sequences which have 70% identical amino acids but which, in addition, however, differ from the C-terminal Hsp70 reference sequence by gaps when aligned. These gaps can occur either in the homologous molecule used according to the invention or in the reference molecule. Alignments, usually by comparison by computer, are known in the state of the art, as are the programs with which such alignments can be carried out. Furthermore, it is preferred that the proteins or the fragments exhibit an amino acid sequence homology to the carboxy-terminal region, i.e. in the region of the amino acids 384-641, of the Hsp70 protein of $\geq$80% and preferably $\geq$90%.

The finding that heat-shock proteins, C-terminal fragments thereof or derivatives derived therefrom induce immunological activities by means of activation of NK-cells even if they do not form complexes with peptides or if they are not presented as tumour cells on the surface of cells has to be considered most surprising. In June 1998 (cf. Srivastava et al., Immunity 8 (1998), 657-665, herein cited as expert opinion), for example, it was still assumed that isolated heat-shock proteins do not exhibit immunogenic effects such as CTL induction (Blachere et al., J. Exp. Med. 186 (1997), 1315-1322) and cannot induce protective immunity against some kind of cancer (Udono and Srivastava, J. Immunol. 152 (1994), 5398-5403). With the present invention it becomes possible to induce an in vitro or in vivo activation of NK-cells which is independent from the patient and which can be used successfully against various diseases, for example, tumour diseases. Moreover, the use of isolated heat-shock protein allows for an improved standardisation of activation processes. The present invention makes it possible to produce unlimited amounts of HCP, whereas in the case of patient-specific preparations of the HSP peptide complexes the amount of HSP is limited by the size of the tumor.

In addition to the above-mentioned findings it is surprising that the use of C-terminal fragments of the Hsp70 protein also leads to the result of the invention. In particular, it was unexpected that the C-terminal apparently exhibits the same three-dimensional structure which is recognized by the NK-cells and which leads to their activation. The possibility of using the C-terminal Hsp70 fragments in the activation of NK-cells also has the advantage that the recombinant production should lead to increased yields in comparison to the recombinant presentation of the whole protein.

The production of derivatives of Hsp70 or its C-terminal fragments, e.g. by peptidomimetics, is for example useful if a rapid degradation of these (poly)peptides in the body is to be avoided. This can play a role e.g. with oral administration of pharmaceutical preparations.

Preferably, the activation comprises the induction of an immune response mediated by NK-cells. Here, it is particularly preferred that the immune response mediated by NK-cells comprises a stimulation of the proliferation of the NK-cells and/or an increase of the cytolytic activity of the NK-cells. (Pharmaceutically) effective amounts of Hsp70 or of fragments or derivatives thereof are used in all of the above-mentioned embodiments so that the desired activation, preferably the immune response, is induced. The immune response is primarily, but not exclusively, directed against such cells expressing Hsp70 or fragments thereof on the cell surface. This includes both human and animal cells. Human or animal cells expressing Hsp70 on the cell surface include, for example, tumour cells and cells from patients with infectious diseases. The cytolytic activity of the NK-cells stimulated by Hsp70 according to the invention is significantly increased so that an immunological elimination of these cells expressing Hsp70 on the cell surface becomes possible.

In a particularly preferred embodiment of the use according to the invention the cytolytic activity against tumour cells and/or cells from patients with infectious diseases is increased.

In another particularly preferred embodiment of the use according to the invention the cytolytic activity against leukaemia cells, lymphoma cells, tumour cells and metastasizing cells of solid tumours and cells from patients with viral, mycotic or bacterial infectious diseases is increased. One example of the treatment of viral diseases is the treatment of HIV infections, an example of a bacterial infection is the treatment of diseases caused by mycobacteria. Solid tumours whose metastatic cells can be treated by the immunological method of the invention include, for example, carcinomas, sarcomas, melanomas, leukaemias and lymphomas. Examples of carcinomas are colon carcinomas and lung carcinomas.

By using a Hsp70 protein, parts of this protein or $\geq$70% sequence homologous proteins according to the invention, cells which have been infected by viruses, bacteria and/or fungi or cells which have been changed by tumours can be lysed. Cells containing antigenic parts of these foreign organisms or parts of tumour cells can also be lysed by means of activated NK-cells by the use of the Hsp70 protein according to the invention.

The invention further relates to a method for ex vivo or in vitro activation of NK-cells, wherein a physiological cell suspension containing NK-cells is mixed with a Hsp70 protein, a C-terminal fragment thereof or a derivative thereof or a protein with an amino acid sequence homology to the C-terminal region (amino acids 384-641) of the Hsp70 protein of ≧70% and incubated to bring about an activation of the NK-cells. The incubation can take place at room temperature, preferably, however, at physiological temperature (37° C.) on a shaker (gentle shaking).

In a preferred embodiment of the method according to the invention the activation comprises a stimulation of the proliferation of the NK-cells and/or an increase in their cytotoxicity. With regard to the preferred target cells for the cytotoxic activity it is referred to the above-mentioned explanations.

In a particularly preferred embodiment of the method of the invention peripheral, monocucleic blood cells (PBMC) or a fraction thereof which contain NK-cells are used as physiological cell suspensions containing NK-cells.

Using appropriate methods, the NK-cells can be obtained from the patients to be treated or from a healthy donor by taking blood. Preferably, buffy-coats (lymphocyte concentrates) containing NK-cells are to be used.

Buffy-coats (lymphocyte concentrates) are taken from patients via the veins and e.g. heparin is added to prevent clotting of the cells. The buffy-coats to which heparin has been added are gathered in a sterile receptacle (usually little plastic bags) and then centrifuged resulting in an accumulation of blood cells (=PBMC, peripheral, mononucleic blood cells, e.g. lymphocytes, erythrocytes, granulocytes, and so on). The lymphocyte concentrate remains sterile in the vessel (plastic bag). In the case of healthy probands a buffy-coat consists of white and red blood cells (lymphocytes, erythrocytes, and so on). In the case of a tumour patient the buffy-coat does not only consist of blood cells but can also contain tumour cells (in the case of leukaemia, e.g. leukaemia cells=blasts; in the case of solid tumours, e.g. metastasized cells).

The buffy-coats containing peripheral, mononucleic blood cells are used in the form of a physiological cell suspension, preferably with heparin added. The heparin prevents an aggregation of the cells.

In another particularly preferred embodiment of the method of the invention the cell suspension further contains human and animal cells expressing Hsp70 on the cell surface. Stimulation of the NK-cells by the Hsp70 protein however, can also take place without target cells (tumour cells, infected cells) that express Hsp70 on the cell surface being present.

In another particularly preferred embodiment of the method tumour cells, cells from patients with infectious diseases are used as human or animal cells.

In another particularly preferred embodiment of the method leukaemia cells, lymphoma cells, metastasizing cells of solid tumours and cells from patients with viral, mycotic or bacterial infectious diseases are used as human or animal cells.

In another preferred embodiment of the method the physiological cell suspension containing the cells and proteins is incubated for at least 3 hours. In this embodiment, in order to increase the cytolytic effect of the natural killer cells, the target cells of the natural killer cells are preferably incubated together with the natural killer cells and the Hsp70 in suspension, preferably for the aforementioned period. Long-term incubations, however, are also possible for at least 4 days. Thus, in another particularly preferred embodiment of the method according to the invention, incubation is carried out for 4 days.

In another preferred embodiment of the use according to the invention or of the method according to the invention a cytokine is used in addition. The cytokine and the NK-cells and/or the heat-shock proteins, fragments or derivatives thereof can be used separately or together in one dose.

In a particularly preferred embodiment of the use or the method an interleukin is used as cytokine. According to the invention, also a combination of interleukins can be used with the Hsp70 protein to further enhance the activation of the NK-cells, e.g. the immune response mediated by the NK-cells or the stimulation of the proliferation of the NK-cells.

In another particularly preferred embodiment of the use or the method according to the invention IL-2, IL-12 and/or IL-15 is used as interleukin.

The invention makes it possible to re-infuse the patient not only with ex-vivo-activated NK-cells, but also to use in vivo NK-cells treated according to the invention due to avoidance of toxic substances, e.g. in combination with a hyperthermia treatment. This embodiment of the invention has a further, invaluable and surprising advantage, i.e. that the target cells, too, e.g. tumour cells which were resistant to the known therapeutic methods, can now be killed immunologically by the cytolytic effect of the NK-cells. Thus, the invention further relates to a method for in-vivo activation of the immune system, wherein a pharmaceutically effective amount of NK-cells activated according to the above-mentioned method is administered to a patient, optionally in combination with or before a pharmaceutically effective amount of a Hsp70 protein, a C-terminal fragment thereof or a derivative thereof or a protein with an amino acid sequence homology to the C-terminal region (amino acids 384-641) of the Hsp70 protein of ≧70%.

If substances are administered together, they may be put together in one container or separately in several containers, whereas in the case of consecutive processing they are kept separately.

If the NK-cells are administered before the Hsp70 proteins, the corresponding time period before administration of the Hsp70 protein should be at least 3-24 hours.

An example of treatment according to the invention is the following: Buffy-coat cells (lymphocyte concentrates) consisting of peripheral, mononucleic blood cells or bone marrow cells and tumour cells from tumour patients, for example leukaemia patients, are subjected to heat treatment in a sterile sealed container, for example a plastic container, with the Hsp70, Hsp70 related protein and/or effective fragments or derivatives thereof in a water bath with temperature control. Both the tumour cells and the NK-cells stimulated by the present treatment are in the container. After completion of the procedure of the invention, the culture solution containing the activated NK-cells and the lysed tumour cells is re-infused into the patient.

According to the invention the NK-cells are optionally present with other peripheral, mononucleic blood cells, for example with erythrocytes and granulocytes and T-cells. Preferably, therefore, the NK-cells are not used alone, but a mixture of the peripheral, mononucleic blood cells is obtained by isolating buffy-coat cells. These accumulations further contain tumour cells in tumour patients which are immunologically eliminated by the method of the invention.

Furthermore, the invention relates to a method for in vivo activation of NK-cells, wherein a patient is given a pharmaceutically effective amount of a Hsp70 protein, a C-terminal fragment thereof or a derivative thereof or a protein with an amino acid sequence homology to the C-terminal region (amino acids 384-641) of ≧70%.

Moreover, the invention relates to a method for the treatment of tumours, cancer diseases and/or infectious diseases, wherein a patient is given a pharmaceutically effective amount of NK-cells activated according to the above-mentioned method of the invention and/or a Hsp70 protein, a C-terminal fragment thereof or a derivative thereof or a protein with an amino acid sequence homology to the C-terminal region (amino acids 384-641) of the Hsp70 protein of ≧70%.

In a preferred embodiment of the method of the invention the tumour is a solid tumour or a metastasis. The treatment strategy particularly aims at the elimination of single-cell metastases which can be eliminated by the method of the invention. An increased activity of Hsp70-specific cells can be achieved by addition of interleukin-2 in a low dosage, for example 100 I.U. The interleukin-2 may, for example, be introduced into the sterile container, e.g. a plastic container, with the Hsp70.

In another preferred embodiment of the invention the cancer disease is leukaemia or a lymphoma.

In another preferred embodiment of the invention the infectious disease has a viral, mycotic or bacterial origin.

The invention further relates to a pharmaceutical preparation, a medical adjuvant, or a medical product containing a Hsp70 protein, a C-terminal fragment thereof or a derivative thereof or a protein with an amino acid sequence homology to the C-terminal region (amino acids 384-641) of the Hsp70 protein of ≧70% and/or of NK-cells activated according to the method of the invention in a therapeutically effective amount as well as optionally common carrier and/or adjuvant substances. Furthermore, a cytokine as defined above is optionally added to the pharmaceutical preparation.

In a preferred embodiment of the pharmaceutical preparation, the medical adjuvant, or the medical product, the protein is present in a concentration of at least 1 µg/ml, preferably up to 1000 µg/ml, preferably $1 \times 10^6$ to $5 \times 10^8$ NK-cells, wherein an amount of 10 µg to 600 µg/ml is preferred.

Examples of suitable pharmaceutically tolerable carriers are known to the person skilled in the art and comprise, for example, phosphate-buffered saline solutions, water, emulsions, such as oil/water emulsions, sterile solutions, and so on. The pharmaceutical compositions (pharmaceutical preparations) containing such carriers may be prepared according to common methods. The pharmaceutical compositions may be administered to the respective individuals in an appropriate dosage. Ways of administration are, for example, intravenous, intraperitoneal, subcutaneous, intramuscular, topic or intradermal. The dosage depends on many factors, e.g. on the patient's size, sex, weight, age as well as the type of the composition specially administered, the kind of administration and so on. In general, the dosage given per month is 10 to 1000 µg. In connection with the intravenous injection of substances of the invention dosages of 10 to 1000 µg are usual. The compositions may be administered locally or systemically. Generally, administration is carried out parenterally. Therefore, the NK-cells treated with Hsp70 according to the invention are preferably injected intravenously. An injection may also be carried out directly into the tumour with an effective amount of NK-cells being injected. Other known types of application are, of course, also possible.

The Hsp70 itself may, for example, be applied with cytokines. One example of application is the injection of the Hsp70 protein, e.g. with cytokines in an intravenous, intramuscular, a subcutaneous or an intraperitoneal way or, also in the sole of the foot.

In another preferred embodiment of the use or the method or the pharmaceutical preparation or the medical product or the medical adjuvant of the invention, the Hsp70 protein is a human protein. The protein of the invention is, for example, of human origin (with the isolation of cell extracts) or exhibits the amino acid sequence of the human Hsp70 protein (e.g. after recombinant production). Animal Hsp70 proteins may, however, also be used.

The Hsp70 protein or the fragments used according to the invention may be produced recombinantly, isolated from cell extracts, or by means of chemical synthesis. Preferably, the Hsp70 protein or its fragment or derivative is a recombinant protein. Such recombinant proteins can be produced according to standard techniques.

Such standard techniques are known to the person skilled in the art (Sambrook et al., ibid. and Ausubel, "Current Protocols in Molecular Biology", Green Publishing Associates and Wiley Interscience, N.Y. (1989)). For the recombinant production of proteins nucleic acid molecules are used which encode the Hsp70 protein or fragments thereof. These may be various nucleic acid molecules, in particular DNA or RNA molecules, for example cDNA, genomic DNA, mRNA and so on. Such nucleic acid molecules may be naturally occurring molecules and/or molecules produced by genetic or chemical synthesis methods. For the production of recombinant proteins, the person skilled in the art uses vectors, particularly plasmids, cosmids, viruses, bacteriophages and other vectors common in genetic engineering (Sambrook et al., ibid.). The nucleic acid molecules contained in the vectors may be linked to regulatory elements which guarantee the expression in prokaryotic or eukaryotic cells. In this context, the term "expression" can mean both transcription and transcription and translation. Regulatory elements comprise promoters, in particular. For the expression of a nucleic acid molecule in prokaryotic cells a range of promoters are at disposal, e.g. the *E. coli* lac- or trp-promoter, the $P_R$- or $P_L$-promoter of the lambda-phage, lacI, lacZ, T3, T7, gpt, and so on. Eukaryotic promoters are, for example, the CMV immediate early promoter, the HSV promoter, the thymidinekinase promoter, the SV40 promoter, LTRs from retroviruses and the mouse metallothionin I-promoter. A variety of expression vectors for the expression in prokaryotic or eukaryotic cells has been described, e.g. for eukaryotes pKK223-3 (Pharmacia Fine Chemicals, Uppsala, Sweden) or GEM1 (Promega Biotec, Madison, Wis., USA), pSV2CAT, pOG44 and for prokaryotes pQE70, pQE60, pBluescript SK, and so on. Apart from promoters these vectors can also contain elements for further enhancement of the transcription, such as the so-called transcription enhancers. Examples are the SV40 enhancer, the polyoma enhancer, the cytomegalovirus early promoter enhancer and adenovirus enhancer. The recombinant proteins may, therefore, be expressed in various prokaryotic or eukaryotic host cells, for example, when the above-described vectors are used. Examples of such host cells are bacterial cells (such as the *E. coli, streptomyces, bacillus, salmonella typhimurium*), fungus cells (such as yeast cells, particularly *saccharomyces cerevisiae*), insect cells (such as *drosophila* or SF9 cells), animal cells (such as CHO or COS cells) or, also, plant cells and so on. Such host cells are cultivated under conditions allowing for the expression of the recombinant protein which may then be gained from the cells and/or from the culture medium. Methods for the expression of foreign protein in various types of host cells as well as for gaining the produced protein are known to the person skilled in the art.

In another preferred embodiment of the use or the method or the pharmaceutical preparation or the medical product or the medical adjuvant of the invention, the Hsp70 protein comprises the C-terminal fragment (amino acids 384 to 561) of the human Hsp70 or the corresponding region of another Hsp70 exhibiting the effects of the invention, or the C-terminal fragment (amino acids 454 to 460) of the human Hsp70. According to the invention it could surprisingly be shown that fragments having this minimal sequence of 7 amino acids (NLLGRFE) are inhibited by antibodies, and NK activation was thus prevented or stopped. The experiments were carded out according to Multhoff et al., J. Immunol. 158 (1997), 4341-4350. The antibody RPN 1197 available from Amersham was used. The 7 amino acids can be flanked by naturally flanking Hsp70 sequences or by other amino acids. The 7 amino acids are preferred to remain in their natural context. When other flanking amino acids are used, the three-dimensional context, in which said 7 amino acids naturally occur, is preferred to be maintained. Within the 7 amino acids further amino acid exchanges can take place as far as the homology of at least 70% is maintained. These exchanges, however, do not comprise an exchange of arginine in position 458 by lysine. This exchange leads to a change in confirmation. Accordingly, exchanges in the region of the 7 amino acids which lead to a change of confirmation are comprised by the invention only if they exhibit the activation properties desired.

The invention further relates to the use of the NK-cells treated according to a method of one or more of the above-mentioned embodiments for therapy of tumour diseases and/or infectious diseases.

In a preferred embodiment of the use of the invention the therapy is carried out by re-infusion of the NK-cells treated.

The aforementioned in vivo methods may also be used as treatment methods for treating the described indicators.

The Figures show:

FIG. 1: Comparison of the proliferating activity of separated NK- (A)- and T (B)-cells which were stimulated at a concentration of 10 µg/ml each either with IL-2(100 IU/ml)-medium or with other recombinant Hsp70 proteins (rHsp70, rHsp70-C$_{tem}$. (amino acids 384-561), rHsp70homC, DnaK, Hsc70 and heat denatured rHsp70) which are suspended in IL-2-medium (100 IU/ml). The phenotypic characteristics of the NK-cells are the following:

CD3: <5%; CD16/CD56: 46-87%; CD94: 60-70%; p58.1 and p58.2: <5% and T-cells: CD3: 85-92%; CD16/CD56: 5-10%; CD94: <29%; p58.1 and p58.2: not tested; p70: not tested, determined by flow cytometry. The proliferation of the cells was determined after 48 hours and after incubation with $^3$H-thymidine (1 µCi/ml) at 37° C. for 18 hours. The relative percentage of the $^3$H-thymidine absorption in NK- (A) and T (B)-cells was compared to the effects of IL-2 alone (100%). The values show average values of four to seven independent experiments ±standard deviation.

Figure 2A:
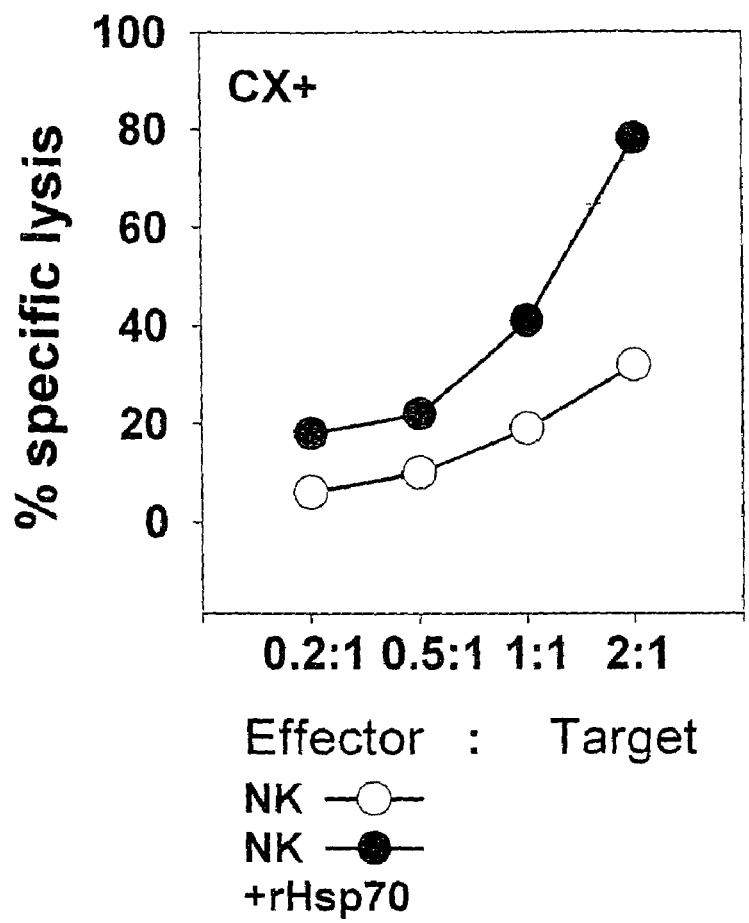
Figure 2B:
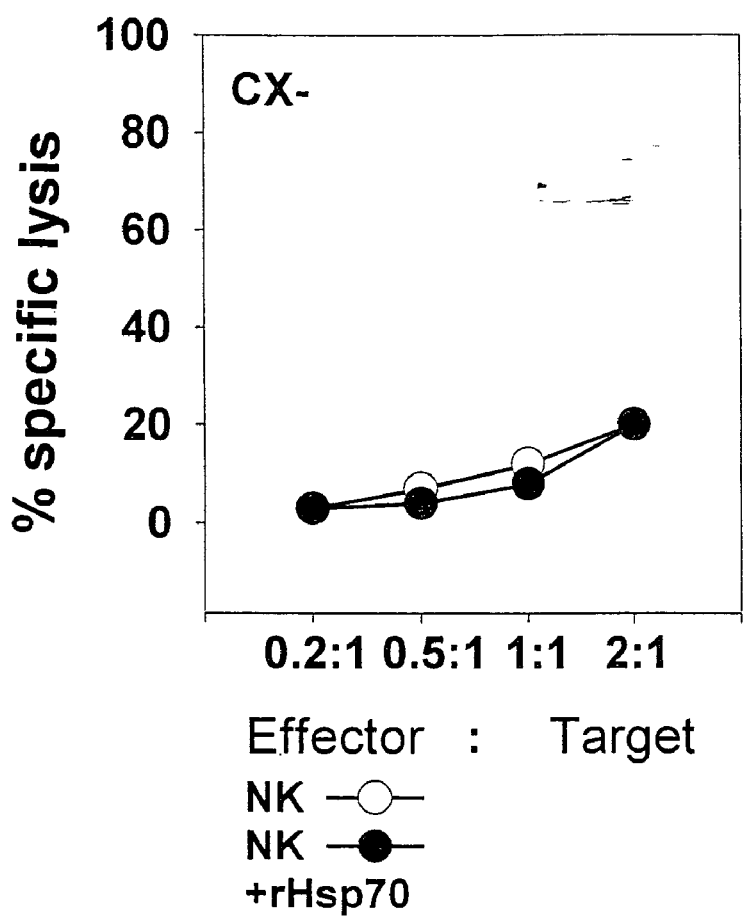

FIG. 2: Comparison of the cytotoxic activity of highly purified NK-cells (CD3: <2%; CD16/CD56; 75-80%; CD94: 65-87%; p58.1 and p58.2: 20-30%; p70: <10%) which either remained untreated (continued lines, empty symbols) or which were pre-incubated after a pre-incubation of the NK-cells with rHsp70 (A)-protein (each 5 µg/ml for 4 days; continued lines, filled in symbols) compared to $^{51}$Cr-labelled tumour target cells CX+ (A) and CX– (B) which are different due to their capability of express plasma membrane. The results are noted as percentage of the specific lysis at various E:T-ratios of 0.2:1 to 2:1. Each point represents the average value of at least three independent experiments ±standard deviation. The percentage of spontaneous release for each tumour target cell line was always below 15%.

Figure 3:
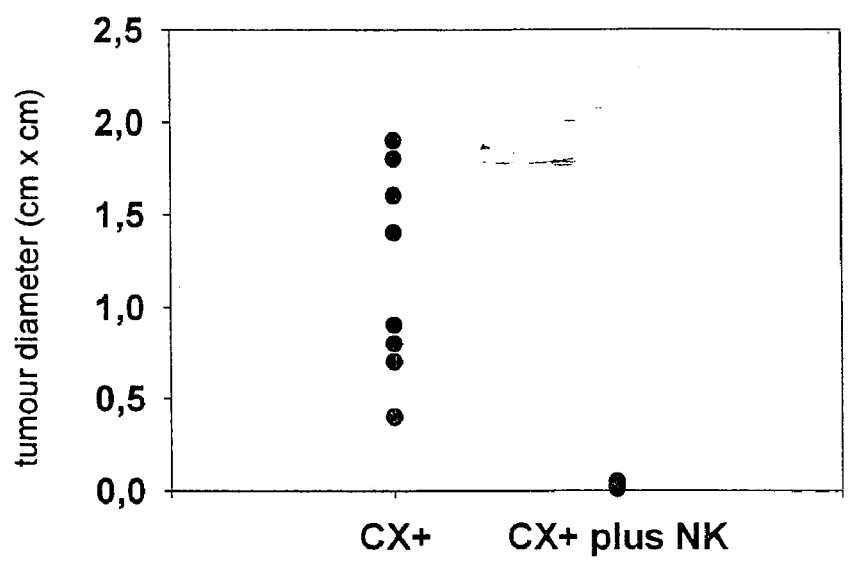

FIG. 3: Tumour growth of CX+ cells carrying Hsp70 in immunodeficient mice. After i.p.-injection of NK-cells the tumour growth is completely inhibited (with i.p.-injection of the tumour cells). The tumour growth was given in cm$^2$. Tumour growth after i.p.-injection of CX+ and NK-cells on day 21.

Figure 4:
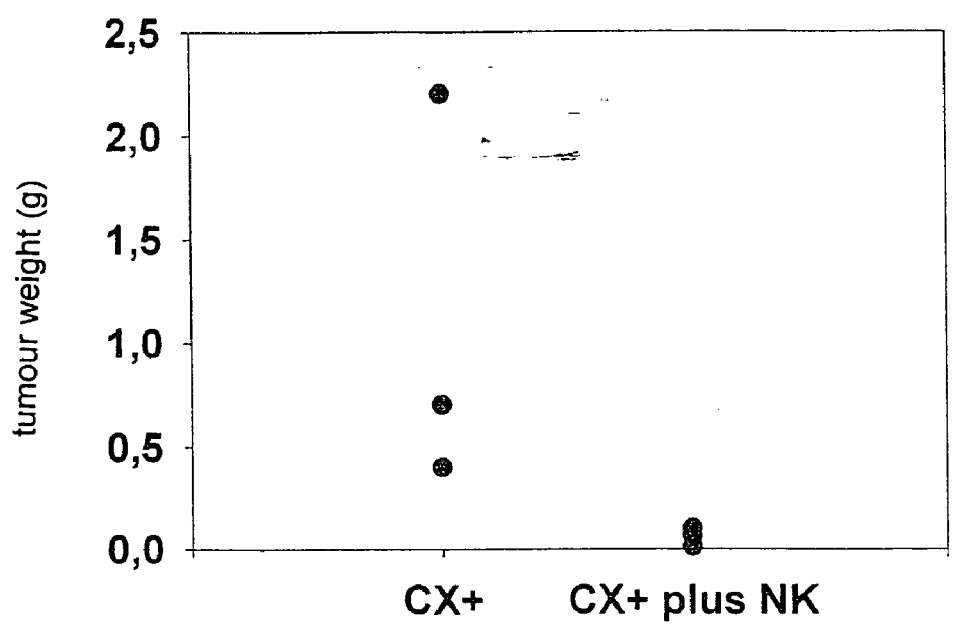

FIG. 4: Tumour growth of CX+ cells carrying Hsp70 in immunodeficient mice. After i.v.-injection of NK-cells the tumour growth is completely inhibited. The tumour growth was measured in gram.

Tumor growth after o.t.-injection of CX+ and i.v.-injection of NK-cells on day 35. The NK-cells inhibit the tumour growth of CX+ cells carrying Hsp70 after 3 or 5 weeks after injection and (see FIG. 3).[1] Both an intraperitoneal and an intravenous application of the NK-cells leads to similar results.

[1] Translators note: sentence incomplete.

FIG. 5: Intact Hsp70-protein with illustration of the C-terminal region

FIG. 6: Illustration of the influence of Hsp70 and/or cytokines on the immune response mediated by NK-cells. The addition of cytokine also leads to a stimulation of T-cells.

Each of the documents cited herein (including instructions of the producers, manuals, etc.) has been incorporated by reference in the description.

The Examples illustrate the invention.

EXAMPLE 1

Increased Proliferation of NK-Cells After Addition of Hsp70

The proliferation of purified NK- and T-cells which were stimulated with the Hsp70 proteins rHsp70, DnaK, Hsc70, rHsp70-C term. and rHsp70homC (amino acids 384-561) was determined in a $^3$H-thymidine absorption standard test (for test conditions see later). Additionally, first, peripheral blood lymphocytes from voluntary human donors were separated in non-adherent CD3+ T-cell and transient (12-24 hours) adherent CD3-(CD16+/CD56+) NK-cell-subpopulations in a multiple-steps method and subsequent 12-hour incubation in an IL-2 containing medium (see 3). The cells were cultivated separately in rIL-2 (100 IU, Chiron, Frankfurt, Germany) containing an RPMI 1640 (Life Technologies, Eggenstein, Germany) medium for 3-4 days. The proliferation was measured as H-3 absorption.

Panning experiments were carried out using human recombinant Hsp70 (rHsp70, SPP-755, StressGen Biotechnologies, Victoria, Canada) and DnaK (Hsp70-homologue obtained from E. coli, SPP-630, StressGen). The proteins were diluted in PBS to a stem concentration of 1 µg/ml and deep frozen in aliquots at −80° C. T-25 culture flasks were incubated with rHsp70 or DnaK proteins (10 µg/ml) diluted in 3 ml icy cold carbonate buffer, pH 9.5, for 12 hours. After blocking non-specific binding sites with PBS/5% FKS a mixture of T- and NK-cells suspended in PBS/1% FKS at a ratio of 1:2 and 2:1 was incubated in the culture flasks for 1 hour at room temperature. Non-adherent cells were obtained from the supernatant fraction after incubation. Adherent cells were obtained by means of sequential washing steps using ice-cold PBS/10% FKS solution. A single, mild washing step was applied to remove lightly-adherent cells, whereas highly-adherent cells were obtained by means of additional stringent washing steps. The cell populations obtained with each step were counted separately and characterised by flow cytometry and phenotype.

The flow cytometry was carried out on an FACScan instrument (Becton Dickinson, Heidelberg, Germany) as described in (4). The percentage of positive-dyed cells was defined as the difference between the number of specifically-dyed, vital (propidiumiodide-negative) cells minus the number of cells which were dyed with the control antibodies corresponding to the isotype. The following antibodies were used for the phenotypic characterisation:

The control antibody corresponding to the isotype (Dianova, Hamburg, Germany; Becton Dickinson, Heidelberg, Germany), CD16 (Dianova, Hamburg, Germany), CD3 (Dianova, Hamburg, Germany).

The ability of T- or NK-cells to proliferate against various Hsp70 proteins was determined in a $^3$H-thymidine absorption standard test. Viable cells ($5 \times 10^4$ cells/100/1) were put on a micro titer plate containing 96 wells with a flat bottom (Greiner, Nürtingen, Germany), wherein a supplemented RPMI 1640-medium with 100 IU IL-2 and various recombinant Hsp70 proteins (rHsp70, DnaK, Hsc70, the constitutive form of Hsp70, purified from bovine brain, SPP-750; Stressgen; rHsp70-C term. sie rek. C-terminal peptide binding domain of Hsp70 (amino acids 384-561), rHsp70homC, the recombinant C-terminal peptide binding domain of Hsp70hom (Hsp70hom is a testis-specific member of the Hsp70 family exhibiting a high homology (94%) to Hsp70, amino acids 384-561) were used. By testing various concentrations of the Hsp 70 proteins (1-200 µg/ml) it was found that a final concentration of 100 µg/ml was ideal for stimulation. A proliferating activity against IL-2 (100 IU) was determined in parallel as a further control. After an incubation period of 24 hours or 48 hours the cells were labelled with $^3$H-thymidine (1 µCi/well) and the total absorption was determined after 18-hour incubation at 37° C. in a fluid scintillation counter (Beckmann Instruments, Munich, Germany). Furthermore, as internal control, the proliferation capacity was determined from the T-lymphocytes taken from the same donor. Using various Hsp70 proteins/fragments in concentrations of 1-200 µg/ml in dose escalation examinations showed that a maximum stimulation of the proliferation capacity could be achieved with 100 µg/ml Hsp70 protein. The proliferation activity of isolated NK- and T-cells was tested after in vitro stimulation with rHsp70, DnaK, Hsc70, rHsp70-C term. or rHsp70homC (amino acids 384-562). As can be seen in FIG. 1A, the NK-cell proliferation by rHsp70 was significantly stimulated. The stimulation by the carboxy-terminal region of Hsp and by rHsp70homC which, in the C-terminal domain with the amino acids 384-561, is 94% identical to Hsp70 is also possible. In contrast, DnaK and Hsc70 did not stimulate the proliferation of NK-cells. Heat denatured rHsp70 lost its stimulatory properties for the proliferation completely.

Figure 1B:
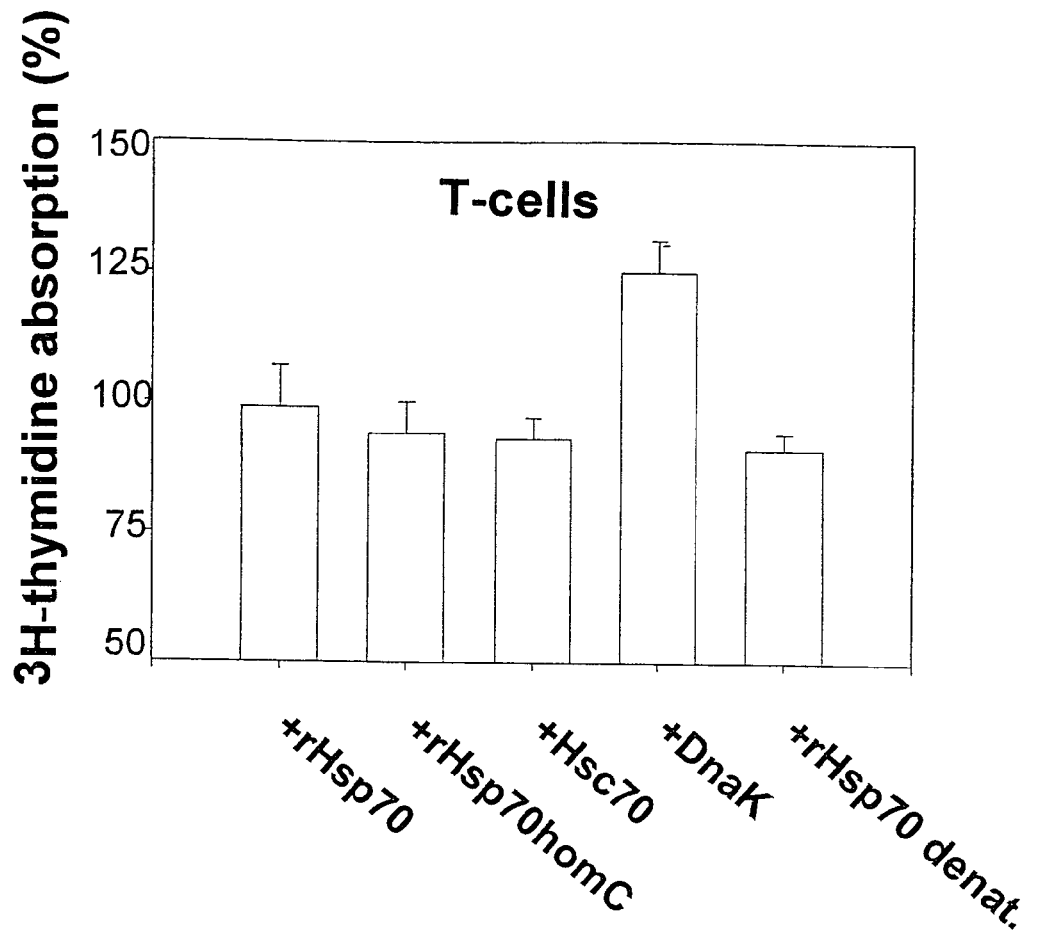

Moreover, it was possible to show that the proliferation of CD3-positive T-lymphocytes could be stimulated by DnaK whereas rHsp70, Hsc70 and rHsp70homC and heat denatured rHsp70 did not show any effect on the proliferation capability of T-cells (FIG. 1B).

Thus, to sum up, a proliferation of NK-cells by recombinant human Hsp70 protein by means of the C-terminal region of Hsp70 (384-561) and rHsp70homC, a protein homologous to the Hsp70, could be induced while a proliferation of the T-cells could selectively be stimulated by bacterial Hsp70 (*E. coli* DnaK).

EXAMPLE 2

Increase of the Cytolytic Activity of NK-Cells after Addition of Hsp70

A functional analysis of the NK-cells using Hsp70-expressing (CX+) and Hsp70-non-expressing (CX−) tumour cells showed that the plasma membrane expression by Hsp70 correlated with an increased sensitivity for the lysis mediated by NK-cells. This lysis mediated by NK-cells can be blocked by pre-incubation of the tumour cell lines with monoclonal antibodies directed against the carboxy-terminal region (amino acids 504-617) of Hsp70 and with the antibody RPN1197 (1, 4). In the following the influence of recombinant Hsp70 protein (rHsp70) on the cytolytic activity of NK-cells for the autologous, Hsp70-expressing (CX+) and Hsp70-non-expressing (CX−) tumour cells was analysed. The results of the cytotoxicity tests using highly-purified NK-cells pre-incubated with Hsp70 protein in a concentration of 5 µg/ml for 4 days are summarised in FIGS. 2A and B. The experimental set-up was the following: For stimulation of the cytotoxic activity NK-cells were incubated with 10 µg/ml rHsp70: The stimulation was repeated after 4 days.

The human, autologous colon carcinoma subcell lines CX+ and CX−, which differ in their Hsp70 expression on the plasma membrane (Multhoff et al., J. Immunol. 158 (1997), 4341), were cultivated in RPMI 1640 medium supplemented with 10% FKS (Life Technologies), 6 mM L-glutamine and antibiotics (100 IU/ml) penicillin and 100 µg/ml streptomycin (Life Technologies). Exponentially growing tumour cells were used as target cells and purified CD3-NK-cells were used as effector cells after cell sorting using a FACStar$^{plus}$ instrument (Becton Dickinson, Heidelberg, Germany). The cytotoxicity mediated by NK-cells was determined by carrying out a 4-hour $^{51}$Cr-radioisotope test (Multhoff et al., J. Immunol. 158 (1997), 4341). The percentage of the specific lysis was calculated as follows: [(experimental release−spontaneous release)−maximum release−spontaneous release]× 100. The spontaneous release of Cr-51 was below 15% in all the experiments.

Surprisingly, it was possible to demonstrate that both the proliferation and the cytolytic activity of NK-cells against Hsp70-expressing tumour cells (CX+) was stimulated when the NK-cells were incubated with rHsp70 protein for at least 4 days. In contrast, NK-cells from the same donor, which were not treated with rHsp70, lost this reactivity after 10 days (dates not shown). The lytic activity of NK-cells not stimulated with rHsp70 was lower compared to NK-cells treated and stimulated with rHsp70 and no significant difference in the lysis could be noted in the lysis of Hsp70-expressing and non-expressing tumour cells.

The present examinations show that the carboxy-terminal part of Hsp70 (amino acids 384-641) is responsible for the stimulation of cytolytic and proliferate function of NK-cells. According to the invention, is was thus possible to demonstrate that particularly the carboxy-terminal part of the Hsp70 protein is effective as stimulating signal for NK-cells which in vitro attack tumour cells specifically expressing the Hsp70.

EXAMPLE 3

Anti-Tumour Effect with NK-Cells Stimulated by Hsp70

For examining the in vivo relevance of NK-cells compared to Hsp70-expressing tumour cells tests were carried out on immunodeficient SCID/beige mice. First, various amounts of tumour cells (CX+ or CX− cells) were injected into SCID/beige mice. An amount of 2.5 mio. cells proved to be the optimal amount of tumour cells to induce tumour growth within a period of 3 to 5 weeks. An i.p. (intraperitoneal) or o.t. (orthotope, i.e. here, in the bowel wall) injection of colon carcinoma cells CX+ and CX− was chosen. The NK-cells were applied after stimulation either i.p. or i.v. (intravenously). As illustrated in FIG. 3, tumour growth could be achieved in all animals both after i.p. and after o.t. injection.

Contrary to the i.p. injection, in addition of growth of a primary tumour after o.t. injection metastasis of the CX+ could also be observed, in particular in spleen and lung (3 in 3 mice after o.t. injection).

Injection of human NK-cells (i.p., but also i.v.), even four days after the injection of tumour cells, leads to a complete inhibition of tumour growth. It is interesting that not only growth of primary tumour cells (in the i.p. region or in the bowels) could be inhibited by NK-cells but also the metastasis of tumours.

These findings clearly show that an immune reconstitution of SCID/beige mice with pre-activated human NK-cells does lead to lysis not only in vitro but also in vivo (in the animal). It is interesting that metastasis by human NK-cells, too, can be suppressed.

The invention claimed is:

1. A method for the ex vivo activation of NK-cells, comprising: contacting NK cells in physiological suspension with an isolated and uncomplexed protein or protein fragment selected from the group consisting of a Hsp70 protein of SEQ ID NO.: 1 and a C-terminal fragment of Hsp70, wherein said fragment comprises amino acids 384-641 of SEQ ID NO.: 1, wherein said isolated protein or fragment, induce an immune response by NK cells, and further said response increases cytolytic activity of the NK cells or stimulates proliferation of the NK cells.

2. The method of claim 1, wherein said activation of said cells further comprises stimulation of proliferation and/or an increase in cytotoxicity.

3. The method of claim 1, wherein said physiological suspension containing NK cells comprises a peripheral mononuclear blood cell fraction or fractions thereof.

4. The method of claim 1, wherein said suspension further comprises cells expressing cell-surface Hsp70.

5. The method of claim 4, wherein said expressing cells comprise diseased cells from a patient.

6. The method of claim 5, wherein said diseased cells are selected from the group consisting of leukemia cells, lymphoma cells, tumor cells, metastasizing cells of solid tumors and cells from a virally, mycotically and/or bacterially infected patient.

7. The method of any one of claims 1-6, wherein said contacting is carried out for at least 3 hours.

8. The method of claim 7, wherein said contacting is carried out for 4 days.

9. The method of claim 7, wherein said contacting further comprise addition of cytokine.

10. The method of claim 9, wherein the cytokine is an interleukin.

11. The method of claim 10, wherein said interleukin is selected from the group consisting of IL-2, IL-12 and IL-15.

12. A method for the in vivo activation of the immune system in a patient in need thereof comprising:
    i) administering to said patient a pharmaceutically effective amount of NK cells obtained by the method of claim 1; and
    ii) optionally administering to said patient, concurrently or subsequently, a pharmaceutically effective amount of an isolated and uncomplexed protein or protein fragment selected from the group consisting of a Hsp70 protein of SEQ ID NO: 1 and a C-terminal fragment of Hsp70, wherein said fragment comprises amino acids 384-641 of SEQ ID NO.: 1 wherein said isolated protein or fragment induces an immune response by NK cells, and wherein said response increases cytolytic activity of the NK cells or stimulates proliferation of the NK cells.

13. The method of claim 12, where said patient is suffering from a disease selected from the group consisting if cancerous, infectious and autoimmune disease.

14. The method of claim 12, further comprising administering a cytokine.

15. The method of claim 14, wherein said cytokine is an interleukin.

16. The method of claim 15, wherein said interleukin is selected from the group consisting of IL-2, IL-12 and IL-15.

17. The method of claim 13, wherein said cancerous disease is selected from the group consisting of tumors, solid tumors, metastic tumors, leukemias and lymphomas.

18. A method for in vivo activation of the immune system in a patient in need thereof comprising administering to said patient a pharmaceutically effective amount of an isolated and uncomplexed protein or protein fragment selected from the group consisting of a Hsp70 protein of SEQ ID NO.: 1 and a C-terminal fragment of Hsp70, wherein said fragment comprises amino acids 384-641 of SEQ ID NO.: 1, wherein said isolated protein or fragment induces an immune response by NK cells, and wherein said response increases cytolytic activity of the NK cells or stimulates proliferation of the NK cells.

19. The method of claim 18, where said patient is suffering from a disease selected from the group consisting of cancerous, infectious and autoimmune disease.

20. The method of claim 18, further comprising administering a cytokine.

21. The method of claim 20, wherein said cytokine is an interleukin.

22. The method of claim 21, wherein said interleukin is selected from the group consisting of IL-2, IL-12 and IL-15.

* * * * *